United States Patent
Bello et al.

(10) Patent No.: US 9,301,032 B1
(45) Date of Patent: Mar. 29, 2016

(54) STETHOSCOPE CHESTPIECE USABLE WITH A PORTABLE ELECTRONIC DEVICE AND RELATED METHODS

(71) Applicants: David Bello, Winter Park, FL (US); Arnold Einhorn, Winter Park, FL (US)

(72) Inventors: David Bello, Winter Park, FL (US); Arnold Einhorn, Winter Park, FL (US)

(73) Assignee: HEARTBUDS, LLC, Winter Park, FL (US)

( * ) Notice: Subject to any disclaimer, the term of this patent is extended or adjusted under 35 U.S.C. 154(b) by 137 days.

(21) Appl. No.: 13/951,812

(22) Filed: Jul. 26, 2013

Related U.S. Application Data

(60) Provisional application No. 61/676,222, filed on Jul. 26, 2012.

(51) Int. Cl.
| | |
|---|---|
| *A61B 7/04* | (2006.01) |
| *H04R 1/46* | (2006.01) |
| *H04R 1/00* | (2006.01) |
| *A61B 7/02* | (2006.01) |
| *A61B 7/00* | (2006.01) |
| *A61B 5/024* | (2006.01) |

(52) U.S. Cl.
CPC .......... *H04R 1/00* (2013.01); *A61B 7/003* (2013.01); *A61B 7/02* (2013.01); *A61B 7/04* (2013.01); *H04R 1/46* (2013.01); *A61B 5/024* (2013.01); *A61B 2562/0204* (2013.01)

(58) Field of Classification Search
None
See application file for complete search history.

(56) References Cited

U.S. PATENT DOCUMENTS

| | | | |
|---|---|---|---|
| 4,362,164 A | 12/1982 | Little et al. | |
| 4,458,778 A | 7/1984 | Bloom | |
| 4,878,501 A * | 11/1989 | Shue | 600/528 |
| 5,747,752 A * | 5/1998 | Selinger | 181/131 |
| 5,852,263 A | 12/1998 | Dieken | |
| 6,475,146 B1 | 11/2002 | Frelburger et al. | |
| 6,610,012 B2 | 8/2003 | Mault | |
| 6,790,178 B1 | 9/2004 | Mault et al. | |
| 8,396,228 B2 * | 3/2013 | Bilan | 381/67 |
| 8,795,438 B2 * | 8/2014 | Rubin et al. | 134/56 R |
| 2004/0076303 A1 * | 4/2004 | Vyshedskly et al. | 381/67 |
| 2007/0058818 A1 * | 3/2007 | Yoshimine | 381/67 |
| 2007/0106179 A1 * | 5/2007 | Bagha et al. | 600/586 |
| 2008/0045161 A1 | 2/2008 | Lee et al. | |

(Continued)

OTHER PUBLICATIONS

Thompson, Jeff, Thinklabs Digital Stethoscopes, Electronic Stethoscope Systems, http://www.thinklabsmedical.com/, Jun. 18, 2013.
Wilton, Pete, Mobile Phones Offer Heart Lifeline, University of Oxford, Sep. 16, 2011, http://www.ox.ac.uk/media/science_blog/160911.html.
Life as a Medical Student: Digital Instruments for Your Phone, Aug. 2011, p. 1-5, http://lifeasamedicalstudent.blogspot.com/2011/08/digital-medical-instruments-for-your.ht.

(Continued)

*Primary Examiner* — Andrew L Sniezek
(74) *Attorney, Agent, or Firm* — Allen Dyer Doppelt Milbrath & Gilchrist

(57) ABSTRACT

An electronic stethoscope chestpiece includes a chestpiece housing having an interior space including a cavity extending from a radially enlarged open end to a radially constricted aperture to form a stethoscope bell. The radially enlarged open end and radially constricted aperture have a common radial axis. Another part of the interior space includes a circuit board positioned above the radially constricted aperture that mechanically supports a headphone connector and a sound detector located at the radially constricted aperture. The circuit board includes a first electrical channel adapted to transmit an electrical signal corresponding to sound in the stethoscope bell to a portable electronic device that records sound and a second electrical channel adapted to allow an audio signal transmitted from the portable electronic device to pass to the headphone connector.

18 Claims, 7 Drawing Sheets

(56) References Cited

U.S. PATENT DOCUMENTS

| | | | |
|---|---|---|---|
| 2008/0146277 A1 | 6/2008 | Anglin et al. | |
| 2010/0081946 A1 | 4/2010 | Garudadri et al. | |
| 2010/0217100 A1 | 8/2010 | LeBoeuf et al. | |
| 2011/0096936 A1* | 4/2011 | Gass | 381/67 |
| 2011/0301435 A1 | 12/2011 | Albert et al. | |
| 2012/0071743 A1 | 3/2012 | Todorov et al. | |
| 2012/0071776 A1 | 3/2012 | Keithline et al. | |
| 2012/0209132 A1 | 8/2012 | Jones et al. | |
| 2013/0116584 A1* | 5/2013 | Kapoor | 600/513 |

OTHER PUBLICATIONS

Brennan, Thomas, Integrating low-cost sensors with mobile phones for remote monitoring of long-term conditions in resource-constrained environments, Welcome Trust / EPSRC Post-doctoral Research Assistant, Institute of Biomedical Engineering, University of Oxford, thomas.brennan@eng.ox.ac.uk.

Kaun, Katherine, A Framework for Automated Hart and Lung Sound Analysis Using a Mobile Telemedicine Platform, Jul. 2010, Massachusetts Institute of Technology.

* cited by examiner

STETHOSCOPE CHESTPIECE USABLE WITH A PORTABLE ELECTRONIC DEVICE AND RELATED METHODS

CROSS-REFERENCE TO RELATED APPLICATION

This claims the benefit of provisional application Ser. No. 61/676,222, filed on Jul. 26, 2012 and titled "Heart Monitor Device, System, and Related Methods," which is incorporated by reference in its entirety.

FIELD OF THE INVENTION

The invention relates to the field of medical instruments and, more particularly, medical instruments that communicate with portable electronic devices.

BACKGROUND

Modern portable electronic devices such as mobile phones, tablet computers, personal digital assistants, and music players are able to store a large amount of data. These devices include an array of functions, including wireless communications capability and they often have computing power than compares to many of the bulky personal computers made in recent years.

Because of this, many people use their portable electronic devices as handheld computers. This is particularly true in the medical field where medical professionals often store and view patient data on a portable electronic device rather than on handwritten charts. Devices that allow patients to record their own physiological data and transmit the data to their physician's computer or portable electronic device now exist. These devices are particularly advantageous because they allow physicians to monitor their patients remotely.

Physicians typically perform auscultation using a stethoscope to listen to the body's internal sounds. This allows the physician to determine whether the patient is having any heart or lung issues. People have developed electronic stethoscopes that allow these sounds to be recorded for subsequent analysis. People have also developed stethoscope-like attachments for portable electronic devices such as smart phones to record these sounds on the deviceS themselves.

There are drawbacks associated with many of the existing stethoscope-like attachments for portable electronic devices. In many cases, the design of the attachment is rudimentary, meaning that it is engineered to serve more as a novelty than as a professional medical instrument. As a result, the sensitivity of these attachments is low and the signals they detect are noisy. Also, because many of them are heavy and bulky, a user cannot easily take them wherever the user goes by, for example, placing the attachment in the user's pocket.

SUMMARY

The various aspects of the invention overcome these drawbacks by employing a handheld and very sensitive stethoscope chestpiece attachment for a portable electronic device. The chestpiece attachment is engineered to minimize noise causing vibrations and includes a sound detector that is positioned to optimize sensitivity for listening to and recording internal body sounds.

According to an apparatus aspect of the invention, an electronic stethoscope chestpiece includes a chestpiece housing having a lower body member and upper body member together defining an exterior surface and an interior space within the exterior surface. The interior space in the lower body member includes a cavity extending from a radially enlarged open end to a radially constricted aperture to form a stethoscope bell. The radially enlarged open end and radially constricted aperture have a common radial axis passing therethrough. The interior space in the upper body member includes a circuit board positioned above the radially constricted aperture that mechanically supports a headphone connector and a sound detector located at the radially constricted aperture. The circuit board includes a first electrical channel adapted to transmit an electrical signal corresponding to sound in the stethoscope bell to a portable electronic device that records sound and a second electrical channel adapted to allow an audio signal transmitted from the portable electronic device to pass to the headphone connector.

According to a system aspect of the invention, a system for performing auscultation includes a chestpiece housing having a lower body member and upper body member defining an exterior surface and an interior space and a stethoscope bell including a cavity recessed into the lower body member from a radially enlarged open end to a radially constricted aperture co-axial with the radially enlarged open end. A sound detector is located at the radially constricted aperture for converting sound in the cavity to an electrical auscultation signal. Electronic circuitry within the chestpiece housing is configured to (a) transmit the auscultation signal to a portable electronic device having a processor, machine readable memory, and a display and (b) transmit the auscultation signal from the portable electronic device to a remote speaker after it is transmitted from the sound detector to the portable electronic device and from the portable electronic device back to the electronic circuitry. Program instructions instruct the portable electronic device to show a graphical image of the auscultation signal on the display and store the auscultation signal in the machine readable memory.

According to a method aspect of the invention, a method of performing auscultation includes placing against a person's body a stethoscope bell of a chestpiece housing having a lower body member and upper body member together defining an exterior surface and an interior space, the stethoscope bell including a cavity recessed into the lower body member from a radially enlarged open end to a radially constricted aperture, the radially enlarged open end and radially constricted aperture having a common vertical axis passing therethrough. The stethoscope bell is positioned over a source of auscultation so that sound enters the cavity and becomes incident on a sound detector located at the radially constricted aperture. An auscultation signal corresponding to the sound from the sound detector is transmitted to a portable electronic device having a processor, machine readable memory, and a display. One can listen to the auscultation signal on a speaker while the sound is incident on the sound detector but after it is transmitted from the sound detector to the portable electronic device and subsequently to the speaker. A graphical image of the electrical auscultation signal is shown on the display and the auscultation signal is stored in the machine readable memory.

These and other objects, aspects, and advantages of the invention will be better appreciated in view of the accompanying drawings and the Detailed Description of Preferred Embodiments.

DETAILED DESCRIPTION OF PREFERRED EMBODIMENTS

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features, steps, etc. are optionally present. When reference is made to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to certain preferred embodiments. This invention may, however, be embodied in many different forms and should not be construed as limited to the embodiments set forth herein. Rather, these embodiments are provided so that this disclosure will convey preferred embodiments of the invention to those skilled in the art.

Figure 1:
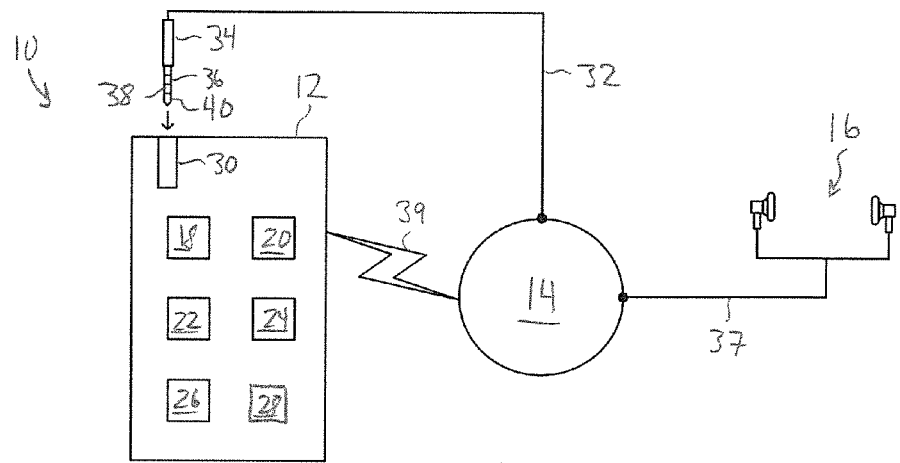
FIG. 1 is a schematic view of a system of performing auscultation, according to a system aspect of the invention.
Figure 2:
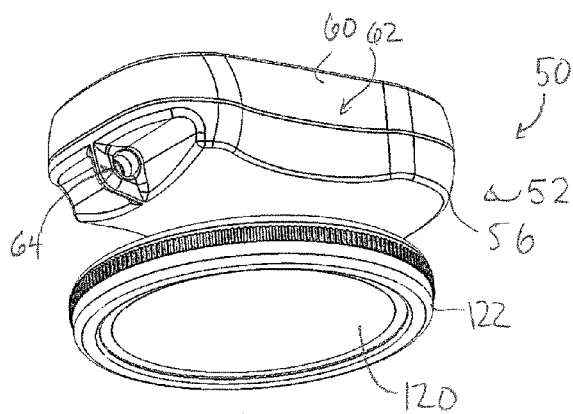
FIG. 2 is bottom side perspective view of a stethoscope chestpiece, according to an apparatus aspect of the invention.
Figure 3:
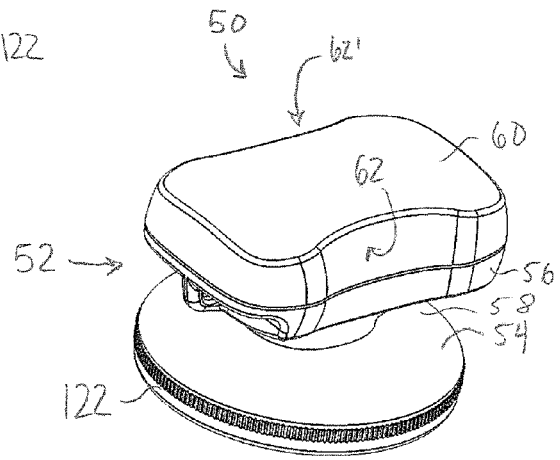
FIG. 3 is a top side perspective view of the stethoscope chestpiece of FIG. 2.
Figure 4:
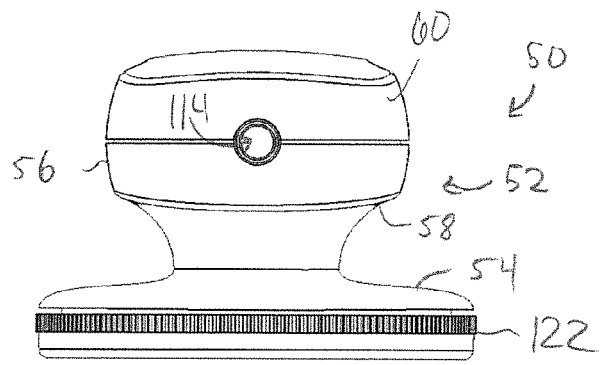
FIG. 4 is a back side plan view of the stethoscope chestpiece of FIG. 2.
Figure 5:
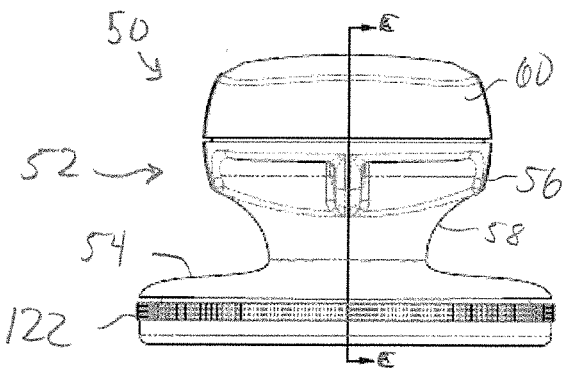
FIG. 5 is a front side plan view of the stethoscope chestpiece of FIG. 2.
Figure 6:
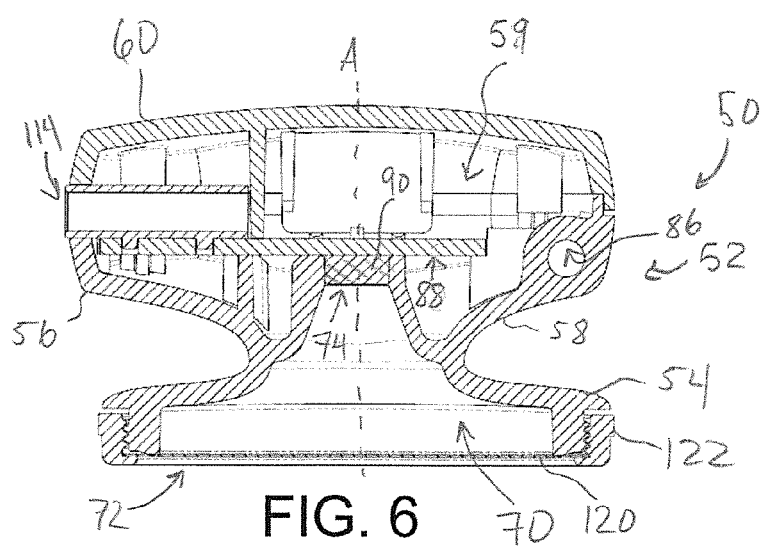
FIG. 6 is a cutaway view of the stethoscope chestpiece of FIG. 2 taken along plane C marked in FIG. 5.
Figure 7:
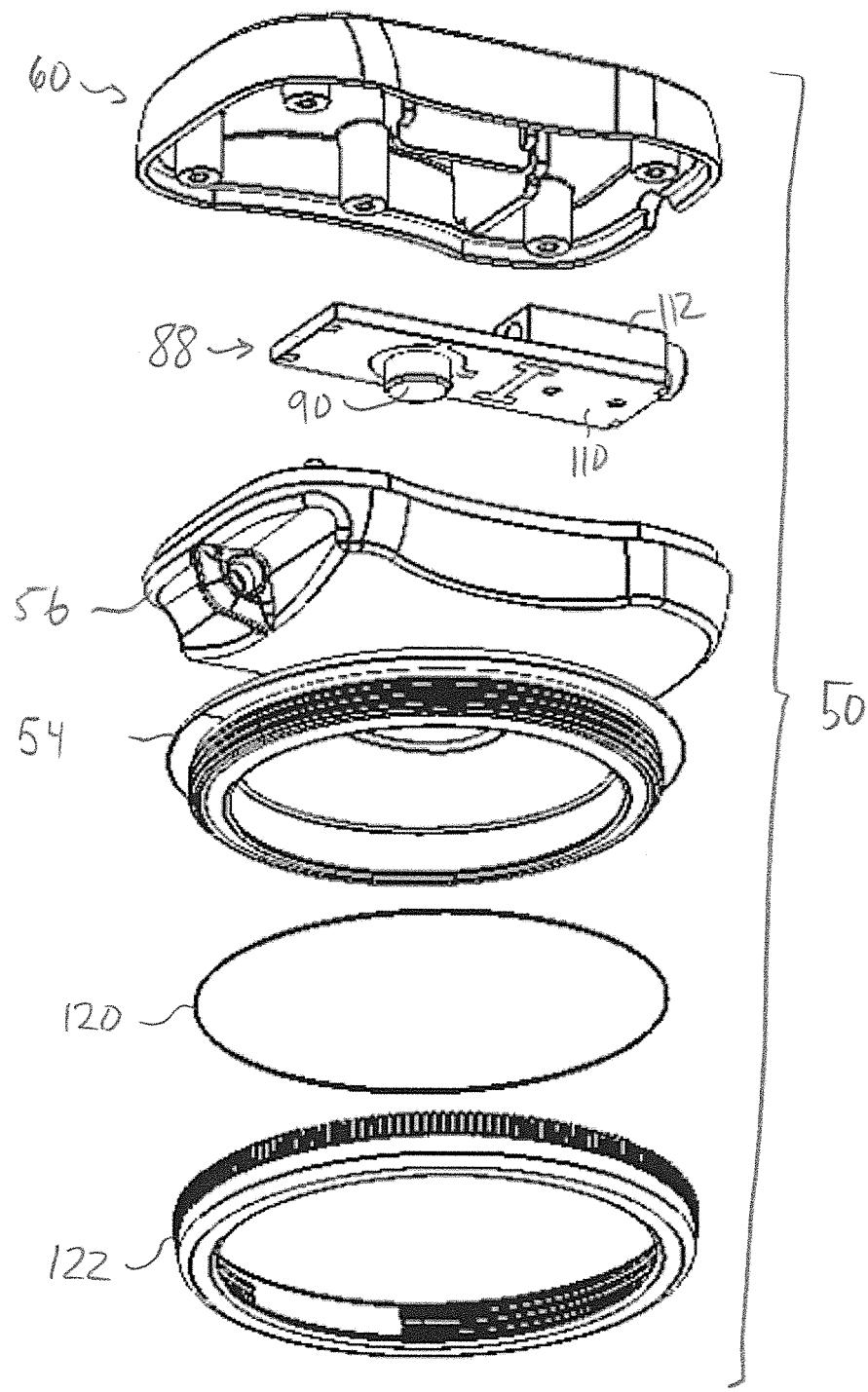
FIG. 7 is an exploded view of the stethoscope chestpiece of FIG. 2.
Figure 8:
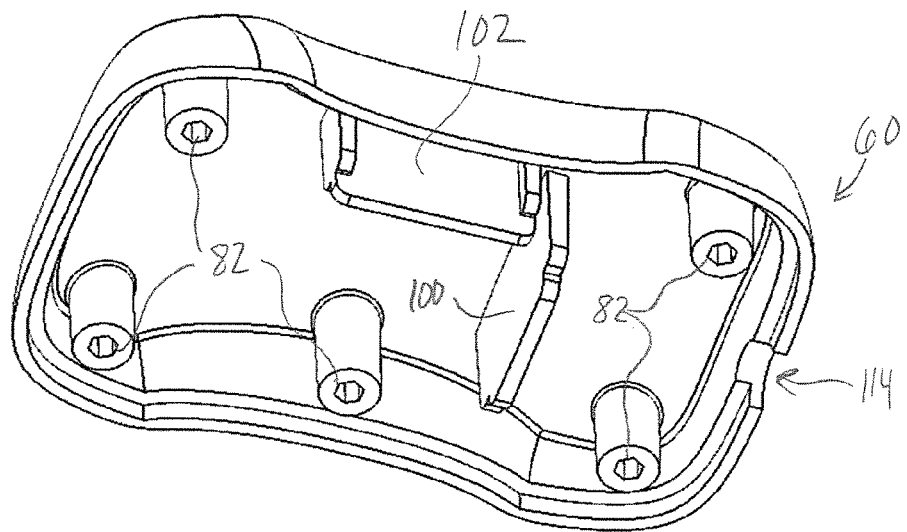
FIG. 8 is a bottom side perspective view of a closure member that is installed on the stethoscope chestpiece of FIG. 2.
Figure 9:
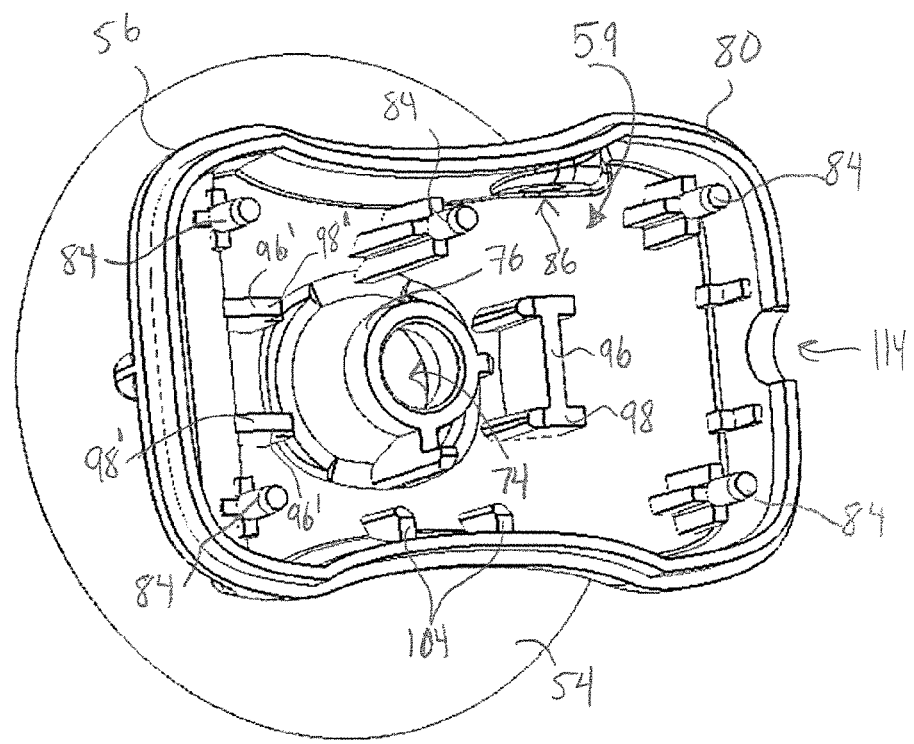
FIG. 9 is a top side perspective view of the stethoscope chestpiece of FIG. 2 with the closure member and electrical components removed to show the interior space within the chestpiece housing.
Figure 10:
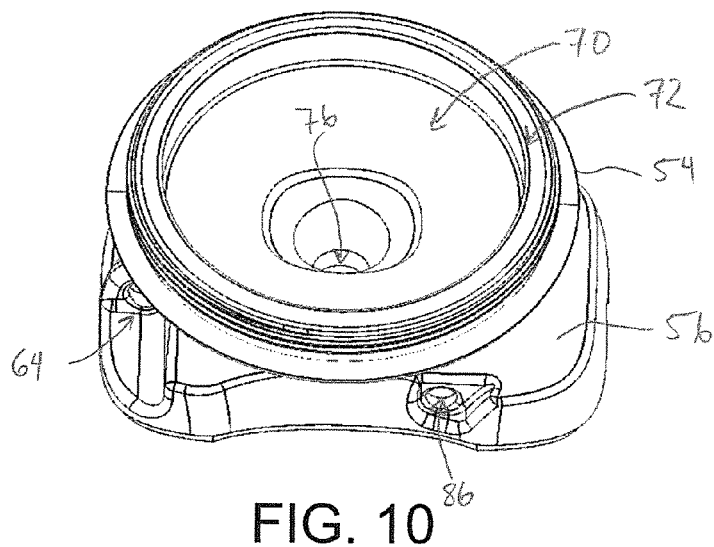
FIG. 10 is a bottom side perspective view of the chestpiece housing of FIG. 2 with a diaphragm and a threaded flange removed to show the cavity.
Figure 11:
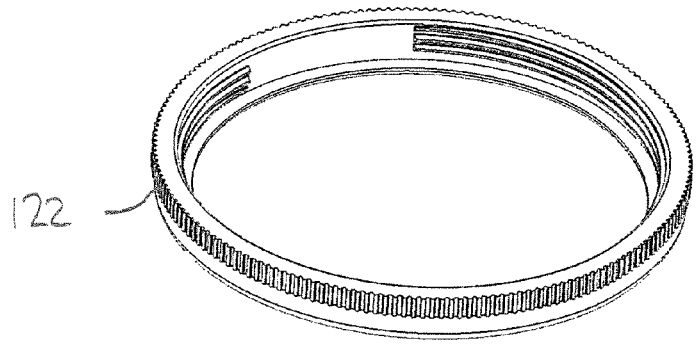
FIG. 11 is a top side perspective view of a threaded flange used to attach the diaphragm to the stethoscope chestpiece housing.
Figure 12:
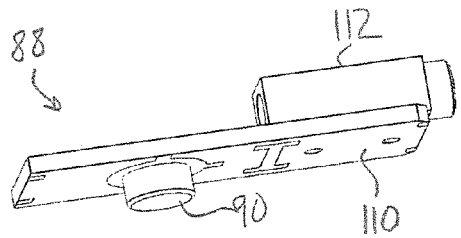
FIG. 12 is a bottom side perspective view of a circuit board assembly used in the stethoscope chestpiece of FIG. 2.

Referring to FIG. 1, a system for performing auscultation 10, in accordance with a system aspect of the invention, includes a portable electronic device 12, a stethoscope chestpiece 14, and an optional remote speaker 16.

The portable electronic device 12 includes a processor 18, memory 20, input/output (I/O) circuitry 22, communications circuitry 24, a display 26, and a user interface 28. It is not necessary for all embodiments of the portable electronic device 12 to include all of these components. One or more of the components may be omitted to combined with other components. The portable electronic device 12 may include other components not shown in FIG. 1, including a power supply, bus, input port, and/or outport port, and/or one or more speakers, among many other components. The components shown in FIG. 1 are included for the sake of brevity only.

The processor 18 is adapted to execute machine readable instructions for controlling the operations of the electronic device 12. The processor 18 also executes the display 26 and processes user input received from the user interface 28.

The memory 20 includes one or more electronic data storage units such as a hard-drive, solid state drive, flash memory, permanent memory, or any combination thereof. Examples of electronic data storage units include cache memory, semi-permanent memory, permanent memory, or any other electronic data storage medium. The memory 20 is adapted to store data used to operate electronic device applications, input data received, auscultation data, communications data, machine readable program instructions, or any other type of data that can be stored electronically.

The I/O circuitry 22 is adapted to convert analog signals and other signals into digital data or vice versa. Digital data is provided to and received from the processor 18, memory 20, or any other component of the portable electronic device 12. Although the I/O circuitry 22 is shown in FIG. 1 as a single component of electronic device 12, the electronic device 12 is not limited to including only a single instance of I/O circuitry 22.

A user provides inputs to the I/O circuitry 22 through the user interface 28, which may include one or more buttons, keypads, dials, touch screens, or any combination thereof. In some embodiments, the portable electronic device 12 includes a capacitive sensor, or a multi-touch capacitive sensor mechanism that senses when a user physically contacts the user interface 28 interface such as a touch screen on the device 12.

The portable electronic device 12 includes output circuitry associated with one or more output devices such as, for example, one or more audio components that are remotely coupled to the device 12. These include a remote speaker 16 and the stethoscope chestpiece 14.

The I/O circuitry 22 includes display circuitry for executing the display 26, which is visible to the user. The display 26 may include a screen incorporated into the portable electronic device 12. The display circuitry preferably includes a coder/decoder (Codec) to convert digital media data into analog signals, including video Codecs, audio Codecs, or any other suitable type of Codec.

The communications circuitry 24 is adapted to connect to a communications network and to transmit communications data from the portable electronic device 12 to other devices connected to the network. The communications circuitry 24 is interfaced with the communications network using any suitable communications protocol such as, for example, Wi-Fi, Bluetooth, radio frequency signals, infrared, GSM, GSM plus EDGE, CDMA, quadband, and other cellular protocols, VOIP, or any other suitable protocol.

An auscultation program is stored on the memory 20 and is adapted to instruct the processor 18 as to how to convert audio signals received from the stethoscope chestpiece 14 into auscultation signal data. The data is preferably stored in the memory 20, displayable on the display 26, and audibly detectable via an audio jack 30. The auscultation program includes machine readable instructions that instruct the portable electronic device 12 how to process the signals it receives from the stethoscope chestpiece 14.

Preferred portable electronic devices 12 will typically have an audio jack 30 that is in data communication relationship with the I/O circuitry 22. The audio jack 30 outputs audio signals to the remote speaker 16, if attached thereto. The audio jack 30 also receives audio signals from a microphone positioned on the stethoscope chestpiece 14. Preferred portable electronic devices include, but are not limited to, mobile phones such as smart phones, personal digital assistant-type devices, tablet-type computers, or any other portable audio player/recorder-type device.

The stethoscope chestpiece 14 is in signal communication with the portable electronic device 12 via an audio cable 32 equipped with an audio connector 34 that mates with the audio jack 30 of the portable electronic device 12. Examples of suitable audio connectors 34 include, but are not limited to, conventional 3.5 mm audio plugs and the like. The audio connector 34 includes a sound detector channel 36, a left audio channel 38, and a right audio channel 40. Each channel is connected to corresponding wiring in the audio cable 32 for transmitting and/or receiving audio signals.

If desired the stethoscope chestpiece 14 may be in signal communication with the portable electronic device 12 via a wireless communications link 39.

The remote speaker 16 is preferably removably connected to the stethoscope chestpiece 14 via another audio cable 37 configured to transmit audio signals from the stethoscope chestpiece 14 to the remote speaker 16. Examples of suitable remote speakers 16 include, but are not limited to, conventional stereo or mono headphones or electronic stethoscope earpieces.

A stethoscope chestpiece 50 in accordance with another embodiment of the invention and that may be used with the auscultation system 10 is generally shown in FIGS. 2-12. The chestpiece 50 is advantageously designed to be very sensitive to body sounds but includes very few parts. This minimizes the number of potential noise creating components and also allows the overall footprint of the chestpiece to be small. Because it's housing is preferably made of molded plastic, it can also be made to be very lightweight. The overall design and construction of the chestpiece 50 make it sensitive enough for professional use but also portable and lightweight enough to transported easily.

The chestpiece 50 includes a chestpiece housing 52 having a lower body member 54 and an upper body member 56. Together, the lower 54 and upper 56 body members define an exterior surface 58 on the exterior of the chestpiece housing 52 and a hollow interior space 59. Although not required, it is preferred that the lower 52 and upper 54 body members are integrally formed as a one-piece item of unitary construction to minimize vibrations. A closure member 60 positioned on top of the upper body member 56 covers the interior space 59.

A pair of opposed indentations 62,62' are formed in the upper body member 56 and closure member 60 so that when they are joined together the indentations 62, 62' form a pair of gripping points that are sized about the size of or slightly larger than a human finger so that a user can easily grip the stethoscope chestpiece 50 by placing one finger in one indentation 62 and another finger of the same hand in the other indentation 62', for example.

A ring 64 is formed along the exterior surface 58 on the upper body member 56. The ring 64 may be used to attach a string or the like thereto so that the user can hang the chestpiece 50 from the user's neck or an upright structure.

The exterior surface 58 emulates the shape of an hourglass between the lower 54 and upper 56 body members. The constricted section of the exterior surface 58 is advantageous because it allows the user to wrap one or more of the audio cables 32,37 therearound for ease of storage.

The lower body member 54 functions as a stethoscope bell. It includes a cavity 70 recessed in the lower body member 54 between a radially enlarged open end 72 and a radially constricted aperture 74, which have a common axis A passing therethrough. The cavity 70 carries sound from the radially enlarged open end 72 to the radially constricted aperture 74. The cavity 70 continues through a raised sound detector mount mount 76 in the interior space 59 on which the radially constricted aperture 74 is formed.

The closure member 60 is attached to the upper body member 58 at a rim 80 along the upper periphery of the upper body member 56 by engaging a plurality of sockets 82 in the closure member 60 with corresponding posts 84 in the upper body member 56.

The audio cable 32 is positioned through an audio cable opening 86 in the housing 52 and into the interior space 59 where it contacts a circuit board assembly 88. The sound detector channel of the audio cable 32 is connected to a sound detector 90, such as a microphone or other sound detecting device, mounted on the circuit board assembly 88. The sound detector 90 is cylindrically shaped and extends downwardly into the radially constricted aperture 74 to provide strong sound sensitivity. It is aligned along the axis A by fitting it tightly within the radially constricted aperture. Sound traveling through the cavity 70 is detected by the sound detector 90 which transmits an electrical signal corresponding to the sound through the sound detector channel of the audio cable 32 to the sound detector channel 36 of the audio connector 34. The sound detector is positioned atop the sound detector mount 76 and is aligned with the axis to provide optimum sensitivity.

A plurality of raised circuit board support structures 96, 96' are formed in the interior space 59. The upper surface 98, 98' of each is substantially coplanar with the sound detector mount 76 so that the circuit board assembly 88 is supported along its length so as to be suspended within the interior space 59. When the closure member 60 is installed on the upper body member 56, a tab 100 that extends downwardly into the interior space 59 from inside the closure member 60 presses against the top of the circuit board assembly 88, which in turn presses against the circuit board support structures 96, 96' to secure the circuit board assembly 88 in place.

The audio cable 32 is prevented from moving around within the interior space 59 by pressing it between a plurality of cooperating ribs, namely an upper rib 102 formed on the inside of the closure member 60 and a pair of corresponding lower ribs 104. When the closure member 60 is installed, the upper rib 102 presses the audio cable 32 against the lower ribs 104. Accordingly, the spacing between the upper 102 and lower ribs 104 is slightly less than the diameter of the audio cable 32.

The closure member is also preferably integrally formed from on-piece unitary construction to minimize vibrations.

The circuit board assembly 88 includes a substantially planar circuit board body 110 that supports the sound detector 90 on one side and an audio jack 112 on the opposite side. The audio jack 112 is preferably a conventional 3.5 mm female audio jack designed to mate with a male 3.5 mm audio plug. This arrangement allows the remote speaker 16 to be optional because the user can simply unplug it from the chestpiece 50. The audio jack 112 is accessible through an audio jack opening 114 formed in the chestpiece housing 50.

If desired, the chestpiece housing 50 may include a diaphragm 120 positioned over the radially enlarged open end 72. The diaphragm 120 is held against the radially enlarged open end 72 by placing it between a threaded flange 122 and a threaded section of the lower body member 54 and screwing on the threaded flange 122.

Figure 13:
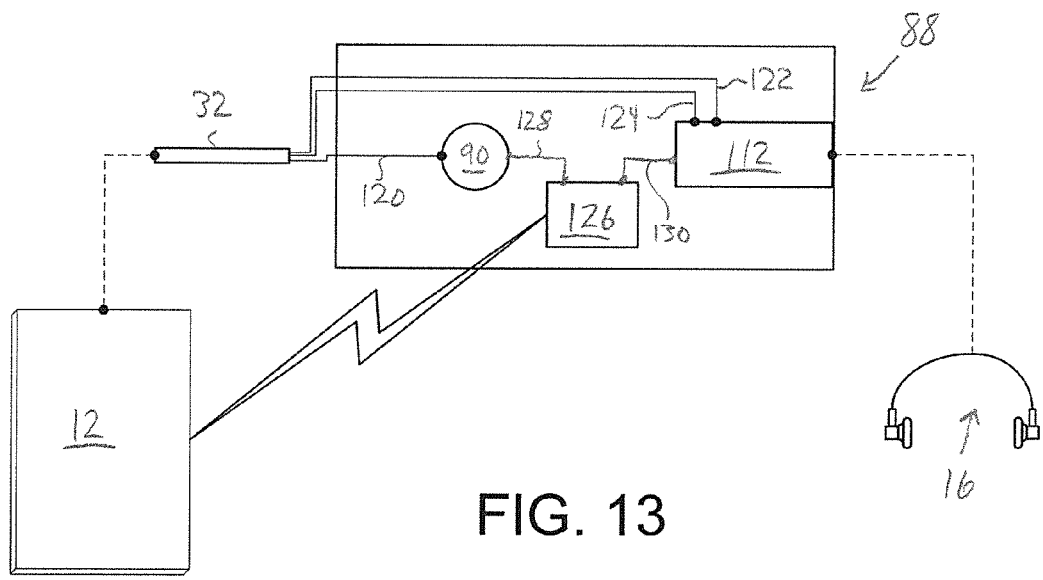
FIG. 13 is a schematic view of the circuit board assembly of FIG. 12.

FIG. 13 is a schematic view of the circuit board assembly 88 and its various preferred connections and components. The sound detector channel 120 of the audio cable 32 is in signal communication with the sound detector 90. When the sound detector 90 detects sound, it transmits an electrical signal corresponding to the sound through the audio cable 32 to the portable electronic device 12, which receives the signal and analyzes the signal using the program instructions. The portable electronic device 12 transmits an audio signal corresponding to the sound through the left and right audio channels 122, 124 to the audio jack 112. This arrangement allows a user to listen to any auscultation signals detected by the sound detector 90 through the remote speaker 16 connected to the audio jack 112.

Optionally, the circuit board assembly 88 includes a wireless transceiver 126 adapted to wirelessly transmit a wireless signal corresponding to sound detected by the sound detector 90 to the portable electronic device 12 and receive a wireless signal corresponding to the sound from the portable electronic device 12. The wireless transceiver 126 is in signal communication with the sound detector 90 via a wiring link 128 therebetween. The wireless transceiver is also in signal communication with the audio jack 112 via another wiring link 130.

The stethoscope chestpiece 50 may optionally include other physiological measurement components besides the sound detector 90. For example, a set of electrocardiogram (ECG) leads can be placed in the vicinity of, or on, the diaphragm 120 to contact the skin of a patient for measuring an ECG signal that is transmitted to the portable electronic device 12. An ultrasound transceiver may be positioned within the cavity 70 for detecting ultrasonic physiological signals that are also transmitted to the portable electronic device 12.

In practice, the portable electronic device 12 receives the electronic signals from the stethoscope chestpiece 50. When the auscultation program is in operation, it instructs the processor 18 as to how to treat the signals. The program 18 instructs the processor to store data representative of the signals in the memory 20. This allows the data to be retrieved at a later date or transmitted to a third party, such as a caregiver or medical personnel, for analysis. The program also instructs the processor 18 to display the data on the display 26.

Figure 14:
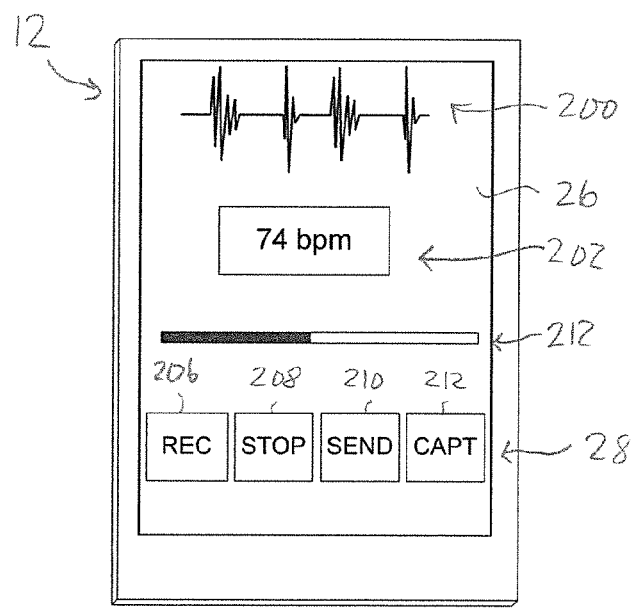
FIG. 14 is a front view of a portable electronic device usable with the system and stethoscope chestpiece, showing an example of data being displayed on the device's display along with some other exemplary functions of the system.

FIG. 14 shows an example of the data being shown on the display 26. In this example, the data are shown numerically or graphically, depending on which display mode is the most amenable to a particular data type. In a first display module 200, the user's heartbeat data obtained from the sound detector 90 is displayed graphically in the form of a phonocardiogram. In a second display module 202, the user's heart rate in beats per minute (bpm) is displayed numerically. Other display modules may be used if additional physiological sensors are employed. For example, display modules for ECG or ultrasound signals may also be shown.

The program is configured to instruct the portable electronic device 12 to store data it receives from the stethoscope chestpiece 50 continuously or over a discrete time period. This functionality is controlled by the user through the user interface 28. The user interface 28 includes one or more control functions that are operable by the user. In the example shown in FIG. 14, the control functions include a record button 206, a stop button 208, a send button 210, and a capture button 212.

When the user activates the record button 206, the program instructs the portable electronic device 12 to begin storing the data in the memory 20 until the time at which the user manipulates the stop button 208.

By manipulating the send button 210, the program instructs the portable electronic device 12 to transmit the data to a portable electronic device via email or other type of electronic data communication mechanism such as SMS and/or MMS messaging.

The program is also configured to retrieve previously recorded data from the memory 20 and either send it to another electronic device or display it on the display 26. When previously recorded data is shown on the display 26, a recording time indicator 212 displays a graphical reference, indicating the time position the data appearing on the screen was recorded relative to the entire time the displayed signal was recorded.

A method of performing auscultation 300, according to a method aspect of the invention is now described with reference to FIG. 15. The method 300 may be performed using the previously described system if desired. A stethoscope bell of a chestpiece housing is initially placed against a person's body (Block 302) and positioned over a source of auscultation (Block 304). The source of auscultation is a source of physiological sound such as the heart or lungs. An auscultation signal corresponding to the sound is transmitted from a sound detector located at a radially constricted aperture of the stethoscope bell to a portable electronic device having a processor, machine readable memory, and a display (Block 306). A person listens to the auscultation signal on a speaker, such as a headphone or the portable electronic device's built-in speaker, while the sound is incident on the sound detector but after it is transmitted from the sound detector to the portable electronic device and subsequently to the speaker (Block 308). A graphical image of the auscultation signal is shown on the display (Block 310) and the auscultation signal is stored in the machine readable memory. This aspect of the method ends at Block 314.

If desired, the data stored on the machine readable memory may be transmitted to a different electronic device, including a computer or mobile communication device such as a phone or tablet. This functionality allows a patient to transmit the auscultation data to medical personnel so that medical personnel can remotely review the data without having the patient visit a physician's office. This aspect of the method, which is described with reference to FIG. 16, continues from Block 314 of FIG. 15.

Figures 15, 16:
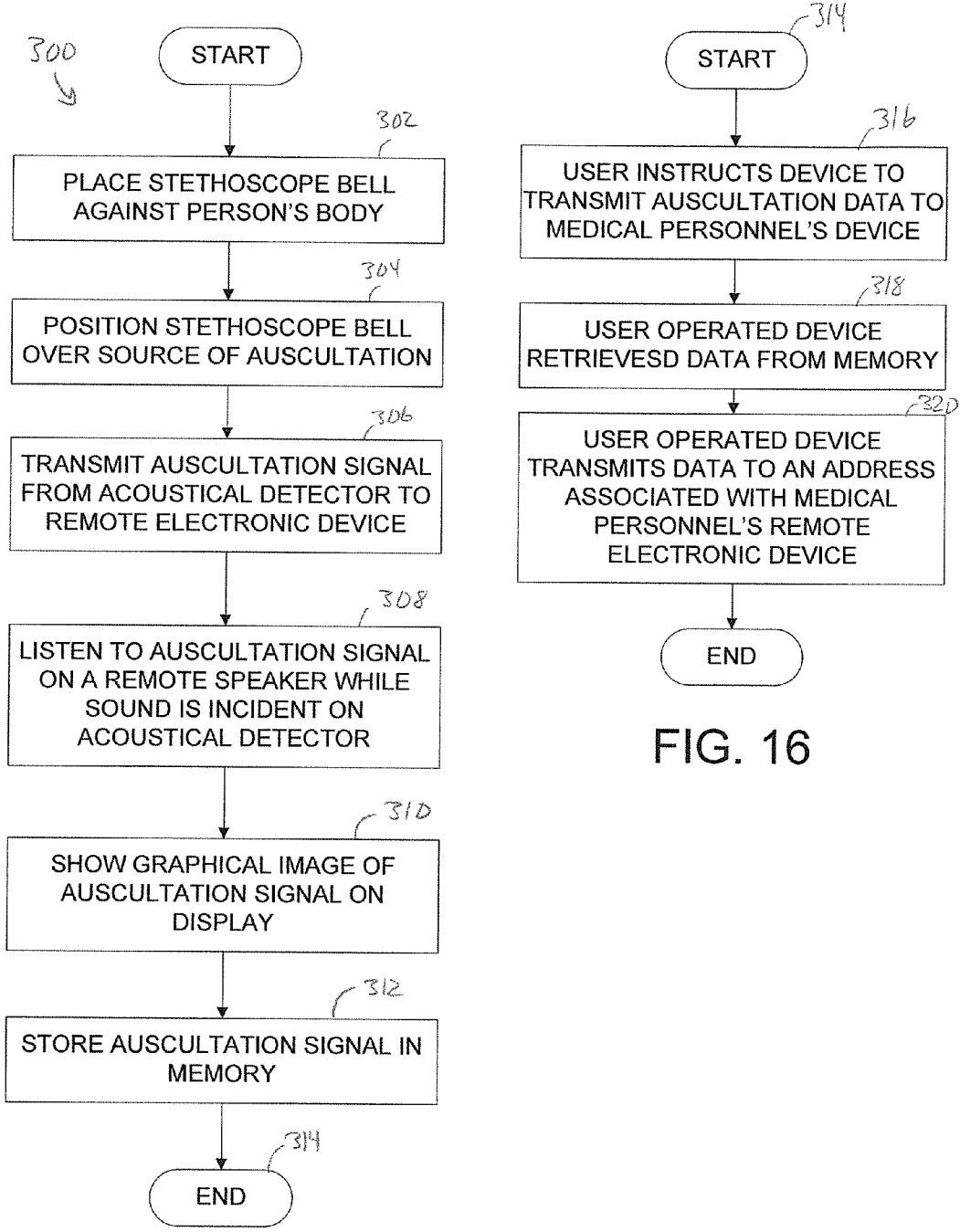
FIG. 15 is flow diagram illustrating a method of performing auscultation, according to a method aspect of the invention.
FIG. 16 is a flow diagram illustrating additional steps that the method illustrated in FIG. 15 may include.

Referring now to FIG. 16, at Block 316 the user instructs the user operated portable electronic device to electronically transmit auscultation data stored in the machine readable memory to a medical personnel operated electronic device. At Block 318, the user operated portable electronic device retrieves the data from the memory. At Block 320, it electronically transmits the data to an address associated with the medical personnel operated electronic device. The address associated with the medical personnel operated electronic device may be any type of address associated with an electronic device such as an email address, telephone, number, messaging address, IP address or the like.

The invention has been described above with reference to preferred embodiments. Unless otherwise defined, all technical terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention.

Accordingly, this invention may be embodied in many different forms and should not be construed as limited to the embodiments set forth herein. Aspects of the invention have been described in some detail, but it will be apparent that various modifications and changes can be made within the spirit and scope of the invention as described in the foregoing specification and as defined in the appended claims.

That which is claimed is:

1. An electronic stethoscope chestpiece comprising:
a chestpiece housing having a lower body member and upper body member together defining an exterior surface and an interior space within the exterior surface;
the interior space in the lower body member including a cavity extending from a radially enlarged open end to a radially constricted aperture to form a stethoscope bell, the radially enlarged open end and radially constricted aperture having a common radial axis passing therethrough;
the interior space in the upper body member including a circuit board positioned above the radially constricted aperture and mechanically supporting a headphone connector and a sound detector located at the radially constricted aperture, the circuit board including a first electrical channel adapted to transmit an electrical signal corresponding to sound in the stethoscope bell to a portable electronic device that records sound and a second electrical channel adapted to allow an audio signal transmitted from the portable electronic device to pass to the headphone connector.

2. The electronic stethoscope chestpiece of claim 1, wherein the exterior surface between the lower and upper body members is peripherally constricted relative to the exterior surface of the lower and upper body members so as to make the exterior surface emulate an hourglass shape in the axial direction.

3. The electronic stethoscope chestpiece of claim 1, wherein the upper body member includes a rim extending horizontally about a periphery thereof and defining an opening in the upper body member for allowing access to the interior space and the chestpiece housing includes a closure member that is removably connected to the rim to close the opening in the upper body member and preclude access to the interior space.

4. The electronic stethoscope chestpiece of claim 1, wherein the exterior surface of the upper body member includes a pair of opposed indentations horizontally spaced from the vertical axis and sized to admit a human finger.

5. The electronic stethoscope chestpiece of claim 1, wherein the lower and upper body members are integrally formed to have one-piece unitary construction.

6. The electronic stethoscope chestpiece of claim 1, further comprising screw threads formed in the lower body member circumscribing the radially enlarged open end, a diaphragm covering the radially enlarged open end, and a threaded flange mated to the lower body member via the screw threads and holding the diaphragm against the radially enlarged open end.

7. The electronic stethoscope chestpiece of claim 1, wherein the sound detector is a microphone positioned within the radially constricted aperture and the axis extends therethrough.

8. The electronic stethoscope chestpiece of claim 1, wherein the interior space is continuous throughout the upper and lower body members.

9. The electronic stethoscope chestpiece of claim 1, wherein a first end of the circuit board is mechanically supported by the radially constricted aperture and a second end of the circuit board is supported by lower body member adjacent an opening in chestpiece housing into which the headphone connector extends.

10. A system for performing auscultation comprising:
a chestpiece housing having a lower body member and upper body member defining an exterior surface and an interior space, a stethoscope bell including a cavity recessed into the lower body member from a radially enlarged open end to a radially constricted aperture coaxial with the radially enlarged open end;
a sound detector located at the radially constricted aperture for converting sound in the cavity to an electrical auscultation signal;
electronic circuitry within the interior space configured to (a) transmit the auscultation signal to a portable electronic device having a processor, machine readable memory, and a display; and (b) transmit the auscultation signal from the portable electronic device to a remote speaker after it is transmitted from the sound detector to the portable electronic device and from the portable electronic device back to the electronic circuitry; and
program instructions for showing a graphical image of the auscultation signal on the display and storing the auscultation signal in the machine readable memory;
wherein the electronic circuitry includes a circuit board positioned in the interior space in the upper body member above the radially constricted aperture, the circuit board mechanically supporting a headphone connector and the sound detector, the circuit board including a first electrical channel adapted to transmit the auscultation signal from the sound detector to the portable electronic device and a second electrical channel adapted to transmit the auscultation signal from the portable electronic device to the remote speaker.

11. The system of claim 10, wherein the exterior surface between the lower and upper body members is peripherally constricted relative to the exterior surface of the lower and upper body members so as to make the exterior surface emulate an hourglass shape in the axial direction.

12. The system of claim 10, wherein the upper body member includes a rim extending horizontally about a periphery thereof and defining an opening in the upper body member for allowing access to the interior space and the stethoscope housing includes a closure member that is removably connected to the rim to close the opening in the upper body member and preclude access to the interior space.

13. The system of claim 10, wherein the exterior surface of the upper body member includes a pair of opposed indentations horizontally spaced from the vertical axis and sized to admit a human finger.

14. The system of claim 10, wherein the lower and upper body members are integrally formed to have one-piece unitary construction.

15. The system of claim 10, wherein the chestpiece housing includes screw threads formed in the lower body member circumscribing the radially enlarged open end, a diaphragm covers the radially enlarged open end, and a threaded flange is mated to the lower body member via the screw threads and holds the diaphragm against the radially enlarged open end.

16. The system of claim 10, wherein the sound detector is a microphone positioned within the radially constricted aperture and the axis extends therethrough.

17. The system of claim 10, wherein the interior space is continuous throughout the upper and lower body members.

18. The system of claim 10, wherein a first end of the circuit board is mechanically supported by the radially constricted aperture and a second end of the circuit board is supported by lower body member adjacent an opening in chestpiece housing into which the headphone connector extends.

* * * * *